United States Patent
Yamaguchi et al.

(10) Patent No.: US 9,390,597 B2
(45) Date of Patent: Jul. 12, 2016

(54) LABORATORY AUTOMATION APPARATUS, AUTOMATED ANALYTICAL APPARATUS AND SYSTEM

(75) Inventors: Shigeki Yamaguchi, Kasumigaura (JP); Hiroshi Ohga, Hitachiomiya (JP); Kenichi Takahashi, Naka (JP); Tatsuya Fukugaki, Hitachinaka (JP); Mitsuru Onuma, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 199 days.

(21) Appl. No.: 13/876,577

(22) PCT Filed: Sep. 2, 2011

(86) PCT No.: PCT/JP2011/004924
§ 371 (c)(1),
(2), (4) Date: Apr. 23, 2013

(87) PCT Pub. No.: WO2012/046382
PCT Pub. Date: Apr. 12, 2012

(65) Prior Publication Data
US 2013/0201019 A1    Aug. 8, 2013

(30) Foreign Application Priority Data
Oct. 5, 2010    (JP) ................................. 2010-225311

(51) Int. Cl.
G06F 11/32    (2006.01)
G08B 5/36    (2006.01)
G01N 35/00    (2006.01)

(52) U.S. Cl.
CPC ............ G08B 5/36 (2013.01); G01N 35/00722 (2013.01); G01N 35/00871 (2013.01);
(Continued)

(58) Field of Classification Search
CPC .................. G01N 35/00594; G01N 35/00841; G01N 35/00851; G01N 35/00712; G01N 2035/00891; G01N 2035/009; G01N 2035/0091; G01N 2035/0097; G06F 11/324; G06F 11/326; B01L 2300/025; B01L 2300/027
USPC ...................... 340/815.45, 540, 691.1, 815.4; 422/400, 509, 62, 50; 714/E11.185, 714/E11.184; 436/43
See application file for complete search history.

(56) References Cited

U.S. PATENT DOCUMENTS 5,584,563 A * 12/1996 Stottmann ........................ 362/85
5,730,939 A *  3/1998 Kurumada et al. ............. 422/67
(Continued)

FOREIGN PATENT DOCUMENTS

| JP | 02-025755 A | 1/1990 |
|---|---|---|
| JP | 03-189562 A | 8/1991 |

(Continued)

*Primary Examiner* — Travis Hunnings
*Assistant Examiner* — Benyam Haile
(74) *Attorney, Agent, or Firm* — Mattingly & Malur, PC (57) ABSTRACT

A laboratory automation system capable of reducing a wasting time of an operator work by giving a notification that enables a device state and a summary of an operator call to be recognized. The laboratory automation system having notifying means such as a display unit or a speaker which can be recognized by the operator distant from the device, includes a notifying unit for calling the operator, and a notifying unit for notifying a status of the device, in which a state device and a summary of the work conducted by the operator can be easily recognized by the combination of notifications of those notifying units.

8 Claims, 6 Drawing Sheets

(52) U.S. Cl.
CPC ........ G06F11/325 (2013.01); *G01N 2035/009* (2013.01); *G01N 2035/0091* (2013.01); *G06F 11/324* (2013.01)

(56) References Cited

U.S. PATENT DOCUMENTS

| | | | |
|---|---|---|---|
| 7,384,601 B2* | 6/2008 | Matsubara | G01N 35/00712 422/62 |
| 2003/0070498 A1* | 4/2003 | Ohyama et al. | 73/863.01 |
| 2005/0053521 A1* | 3/2005 | Hirayama | 422/67 |
| 2008/0299007 A1* | 12/2008 | Noguchi | B01L 9/06 422/65 |
| 2011/0077871 A1* | 3/2011 | Fukuma et al. | 702/21 |

FOREIGN PATENT DOCUMENTS

| | | |
|---|---|---|
| JP | 06-213902 A | 8/1994 |
| JP | 08-262031 A | 10/1996 |
| JP | 2000-32183 A | 11/2000 |
| JP | 2009-264884 A | 11/2009 |
| JP | 2010-217147 A | 9/2010 |

* cited by examiner

| | DEVICE STATE | CALL NOTIFICATION UNIT | STATUS NOTIFICATION UNIT | | |
|---|---|---|---|---|---|
| | | CALL LAMP (ORANGE) | OPERATION LAMP (GREEN) | SUSPENSION LAMP (YELLOW) | STOP LAMP (WHITE) |
| 201 | INITIALIZING STATE | OFF | OFF | OFF | BLINKING |
| 202 | STOP STATE | OFF | OFF | OFF | ON |
| 203 | RESET STATE | OFF | BLINKING | OFF | OFF |
| 204 | OPERATING STATE | OFF | ON | OFF | OFF |
| 205 | SUSPENSION STATE | OFF | OFF | ON | OFF |
| 206 | DEVICE STOP DUE TO ERROR | ON | OFF | OFF | ON |
| 207 | SAMPLE ERROR | ON | ON | OFF | OFF |
| 208 | THE SMALL NUMBER OF CONSUMABLES (DEVICE OPERATION) | ON | ON | OFF | OFF |
| 209 | NO CONSUMABLES (DEVICE SUSPENSION) | ON | OFF | ON | OFF |

|   | MODULE 1 | LIGHTING LAMP | MODULE 2 | LIGHTING LAMP | STATE |
|---|---|---|---|---|---|
| 301 | DISPENSING MODULE 150 | CALL LAMP 7 | STORAGE MODULE 180 | CALL LAMP 7 | SAMPLE SHORTAGE |
| 302 | DISPENSING MODULE 150 | CALL LAMP 7 | INPUT MODULE 110 | CALL LAMP 7 | DISPENSING NOZZLE CLOGGING OCCURRENCE |
| 303 | DISPENSING MODULE 150 | CALL LAMP 7, SUSPENSION LAMP 9 | BAR CODE ATTACHMENT MODULE 130 | CALL LAMP 7, SUSPENSION LAMP 9 | NO REMAINING BAR CODE LABELS |
| 304 | DISPENSING MODULE 150 | CALL LAMP 7, SUSPENSION LAMP 9 | CAP SUPPLY MODULE 140 | CALL LAMP 7, SUSPENSION LAMP 9 | NO REMAINING SAMPLE CAPS |
| 305 | CLOSING MODULE 150 | CALL LAMP 7 | STORAGE MODULE 180 | CALL LAMP 7 | BAR CODE READ ERROR |

LABORATORY AUTOMATION APPARATUS, AUTOMATED ANALYTICAL APPARATUS AND SYSTEM

TECHNICAL FIELD

The present invention relates to a laboratory automation system that automates a pre-analytical process of a sample for analyzing a biological sample such as blood or urine, an automated analytical system that analyzes the biological sample that has been subjected to the pre-analytical process, and a unit configuring those systems.

BACKGROUND ART

The laboratory automation system is a system that automates a pre-process of a sample such as centrifugation of the sample, cap removal, dispensation, and labeling of identification information among works to be conducted in a clinical laboratory. In the laboratory automation system, in order to enhance the work efficiency of an operator who operates the device, a variety of improvements are conducted. One of the improvements is notifying means for notifying the operator of information.

Patent literature 1 discloses informing means for information that an emergency sample has been input, and the pre-processing has been finished as needed.

Also, Patent Literature 1 discloses that in displaying a generated alarm on an operation screen, the alarm is sorted into three stages of an emergency alarm level, an attention alarm level, and a caution alarm level, and displayed in distinction.

CITATION LIST

Patent Literature

Patent Literature 1: Japanese Unexamined Patent Application Publication No. 2009-264884
Patent Literature 2: Japanese Unexamined Patent Application Publication No. Hei 8 (1996)-262031

SUMMARY OF INVENTION

Technical Problem

In order to notify that the device needs to be subjected to some treatment by the operator, display on the operation screen, the provision of a display lamp, or the provision of a speaker that generates a notice sound is conducted. However, in order that the operator knows detailed notice contents, there is a need to confirm the alarm contents actually displayed on the operation screen. Therefore, if the operator knows through the informing unit that some treatment is required, the operator needs to come near the device, confirms, on the operation screen, the alarm contents and whether the treatment needs to be urgently conducted, or not. If the treatment needs to be urgently conducted, there is a need to prepare for the treatment (replenishment of consumables).

In order that the operator distant from the device identifiers whether the emergency intervention of the operator is required, or not, the operator needs to be able to understand the alarm generated contents. However, in order that the operator understands a large number of alarm contents occurring in the complicated device or system, a complicated informing unit is required.

Patent Literature 1 discloses a device that informs the operator of a state of the emergency sample by the aid of the informing unit such as a display lamp or a speaker. However, there is no disclosure that the alarm contents are informed the operator of when an alarm or the like occurs.

Also, in the device disclosed in Patent Literature 2, although the generated alarm is sorted for each level, and displayed, because the display is displayed by an operation unit PC screen or print, the operator still has to go near the device, and confirm the alarm contents. Also, the displayed alarm level is sorted on the basis of an alarm importance or a countermeasure urgency. However, the generated alarm contents cannot be understood by the operator distant from the device.

Also, in order to notify the operator apart from the device of a large volume of information in the conventional art, it is conceivable to use a large-sized liquid crystal panel, or to increase the kinds of sounds to be reproduced in order to call the operator. However, the large-sized liquid crystal display is expensive, and leads to an increase in the costs of the device. Also, when the kinds of sounds are increased, not only the costs are increased by a complicated control, but also a burden is imposed on the operator for picking up many kinds of sounds. Also, the operator may not be aware of the notice of sound because of noise depending on the environment.

An object of the present invention is to provide a laboratory automation system capable of reducing a wasting time of the operator's work by making a display that enables what kind of operator's work the device needs to be recognized at a glance even from a location apart from the device, inexpensively with the use of an illuminator such as an LED.

Solution to Problem

The laboratory automation system that achieves the above object has the following features.

That is, there is provided a laboratory automation device or an automated analytical device, which include: a notifying unit having a status notifying unit that notifies a consumables state of the device or a device state, and a call notification unit that notifies a need of an operator's call to the device; and a notification control unit that allows the status notifying unit or the call notification unit to give notification one by one, or at the same time in plurality.

Advantageous Effects of Invention

According to the present invention, with the provision of the above configuration, an operating status of the device, the need of processing by the operator, and its contents can be confirmed even at a location distant from the device at a glance. As a result, a time for confirmation is reduced to improve the work efficiency. Also, because the degree of need of the intervention by the operator can be confirmed by the notifying unit, if the operator executes a work in parallel to another work, a treatment of the device and the priority of another work are compared with each other, and the work can be executed in an appropriate order from the work to be prioritized.

DESCRIPTION OF EMBODIMENTS

Hereinafter, embodiments of the present invention will be described in detail with reference to the drawings.

Figure 1:
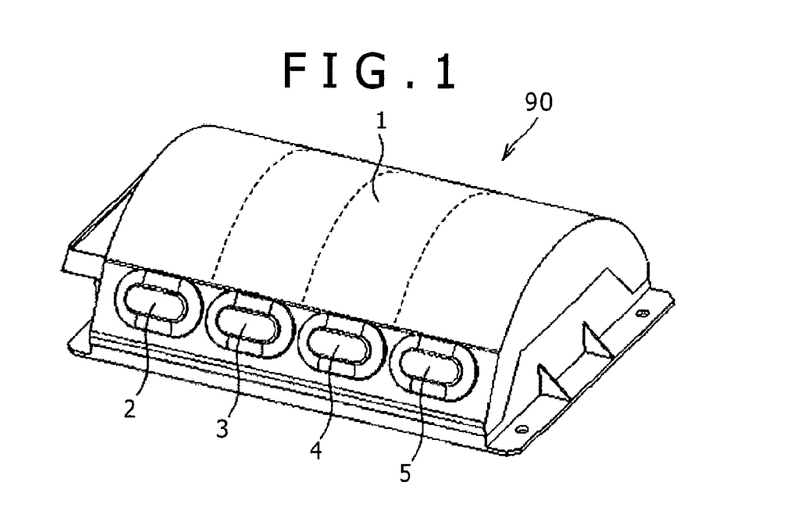
FIG. 1 illustrates a display lamp and a switch unit.
Figure 2:
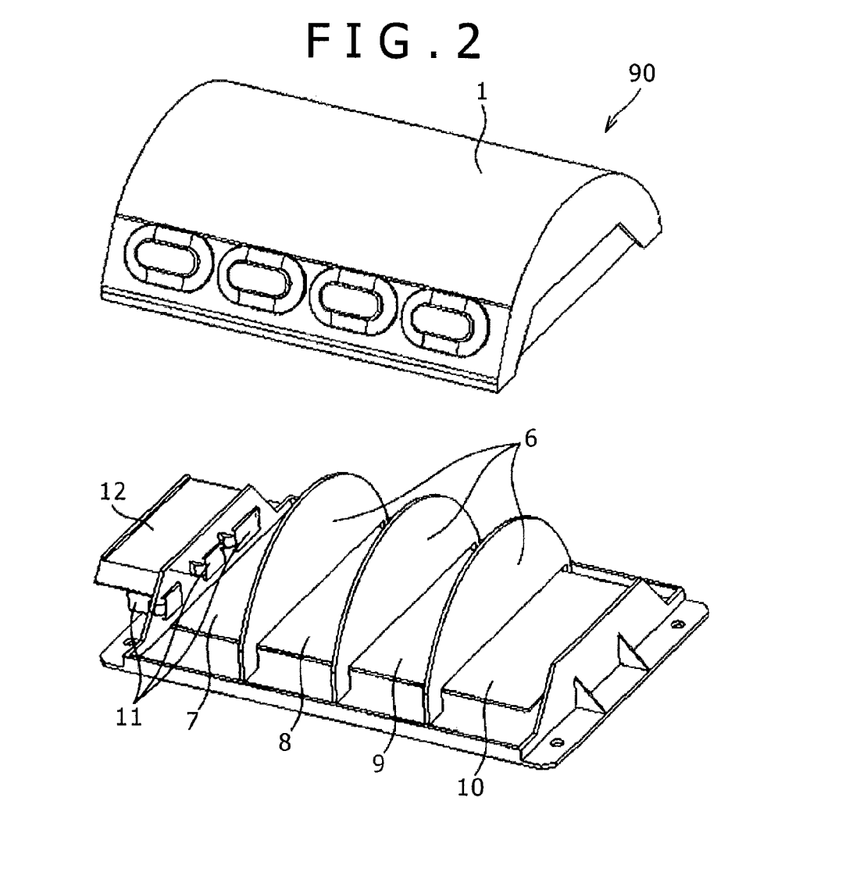
FIG. 2 is an exploded diagram of the display lamp.
Figure 3:
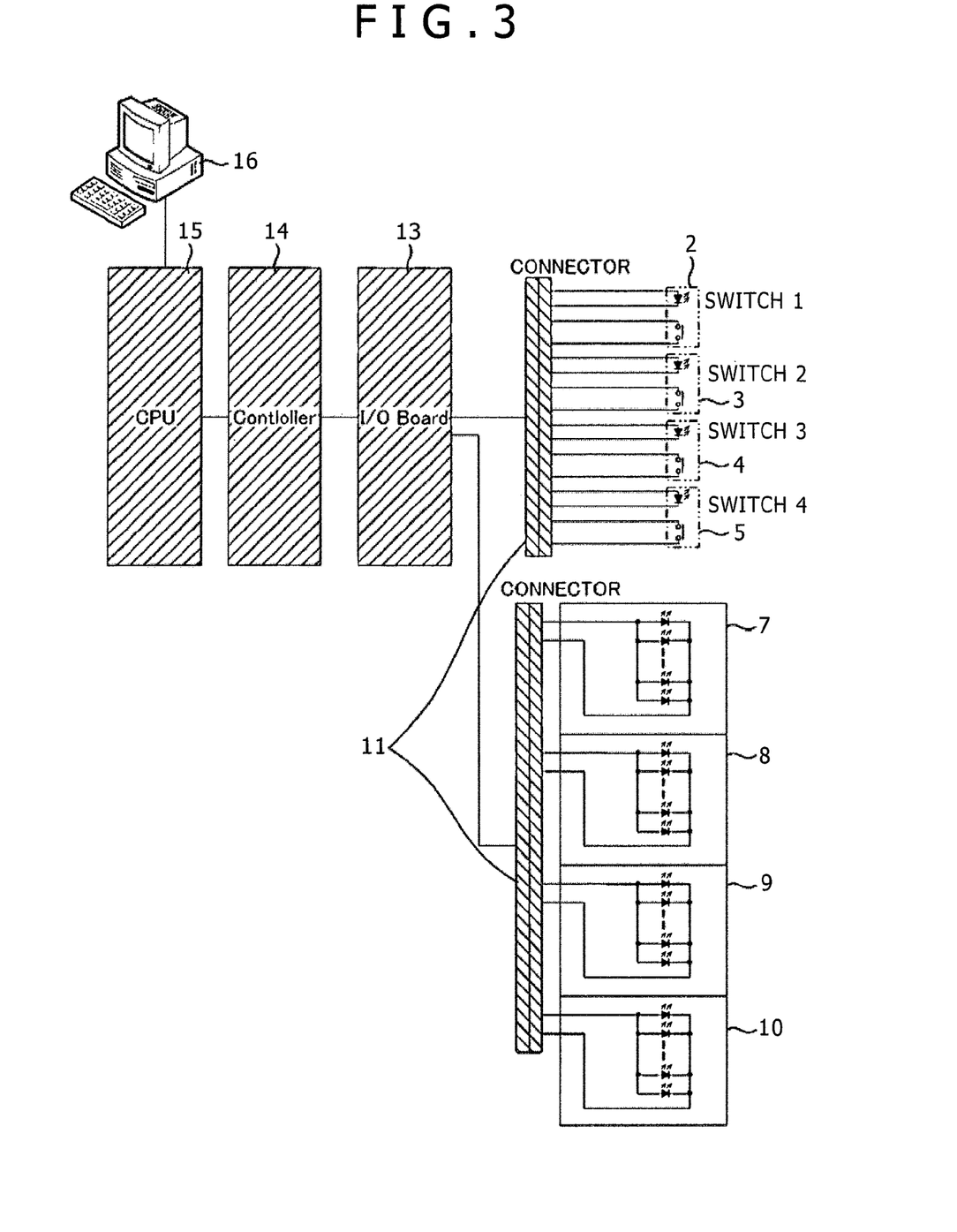
FIG. 3 is an electric block diagram of FIG. 1.

FIG. 1 illustrates a configuration example of a display lamp and a switch unit in a laboratory automation system according to an embodiment of the present invention. FIG. 2 is an exploded view of FIG. 1. FIG. 3 illustrates a configuration example of an electric block diagram of FIG. 1.

FIG. 1 illustrates a display lamp and a switch unit. A switch is disposed below a display unit cover 1, and divided into a call clear switch 2, a start switch 3, a suspension switch 4, and a stop switch 5, and the switches and LEDs are provided therein.

FIG. 2 illustrates an exploded view of FIG. 1. LED blocks are provided inside of the display unit cover 1. The LEDs each emitting a different color light is mounted on a printed circuit board. A left end thereof is a call notification unit in which a call lamp 7 is provided. A status notifying unit is present at a right side of the call notification unit, and includes an operation lamp 8, a suspension lamp 9, and a stop lamp 10. Partition plates 6 of light are provided to prevent the light from being leaked between the respective LED blocks. This embodiment will be described assuming that the call lamp 7 is orange and located on the left side of a display lamp 90, the operation lamp 8 is green and located second from the left of the display lamp 90, and the suspension lamp 9 is yellow and located third from the left of the display lamp 90, and the stop lamp 10 is white and located at a left end of the display lamp 90.

Connectors 11 are connected to lines of power supply to the call clear switch 2, the start switch 3, the suspension switch 4, the stop switch 5, the call lamp 7, the operation lamp 8, the suspension lamp 9, and the stop lamp 10, and signal input/output.

A waterproof cover 12 is furnished for the purpose of preventing the connectors 11 from being exposed to liquid to cause a failure due to short-circuit between the lines within the connectors 11 when the operator spills liquid from the display lamp 90 and an upper portion of the switch unit in error.

In the embodiment, the eliminator is described as the LED, but the present invention is not limited to the LED. For example, the illuminator includes illuminators such an electric bulb or an EL (electro luminescence) illuminator.

Subsequently, FIG. 3 will be described. FIG. 3 illustrates a configuration example of an electric block diagram of FIG. 1.

The switches of the call clear switch 2, the start switch 3, the suspension switch 4, and the stop switch 5 are identical with those described above, and in FIG. 3, an internal structure thereof is represented by electric symbols. Also, the call lamp 7, the operation lamp 8, the suspension lamp 9, and the stop lamp 10 are identical with those described above, and an internal structure thereof is represented by electric symbols.

An I/O board 13 converts a signal into an electric signal such as an ON of OFF signal by closing or opening contacts of the respective switches. Also, the I/O board 13 controls on or off operation of the LEDs installed in the respective switches. Also, the I/O board 13 controls the on or off operation of the LED blocks for the respective lamps.

A control unit 14 transmits a signal to the I/O board 13 according to an instruction from a CPU 15 to control the on or off of the LEDs of the respective switches. Also, the control unit 14 controls the on or off of the LED blocks for the respective lamps.

The signal obtained by converting a contact state of the respective switch into the electric signal by the I/O board 13 is transmitted to the CPU 15 through the control unit 14, and processed.

A host computer 16 can communicate with the CPU 15 by electric communication means, and collects information on the switch contact states of the respective switches transmitted from the CPU 15, and on/off of the LED installed in the respective switches. Also, the host computer 16 collects the on/off information on the LED blocks for the respective lamps.

Subsequently, the operation of the display lamp according to this embodiment will be described.

The call lamp 7 is a call notification unit that executes a display in order that the device calls the operator, and notifies the operator that a call occurs to request an intervention of the operator though lighting or blinking. In this embodiment, the illuminator is used, but a notification may be conducted by sound.

The operation lamp 8, the suspension lamp 9, and the stop lamp 10 are portions for displaying the status of the device, and notify in which state of the operation state, the suspension state, and the stop state the device is.

In this embodiment, the call notification unit and the status notifying unit are installed together in one display unit, and mounted on the device. Alternatively, those notifying units may be mounted on the device as separate notifying units.

Figure 4:
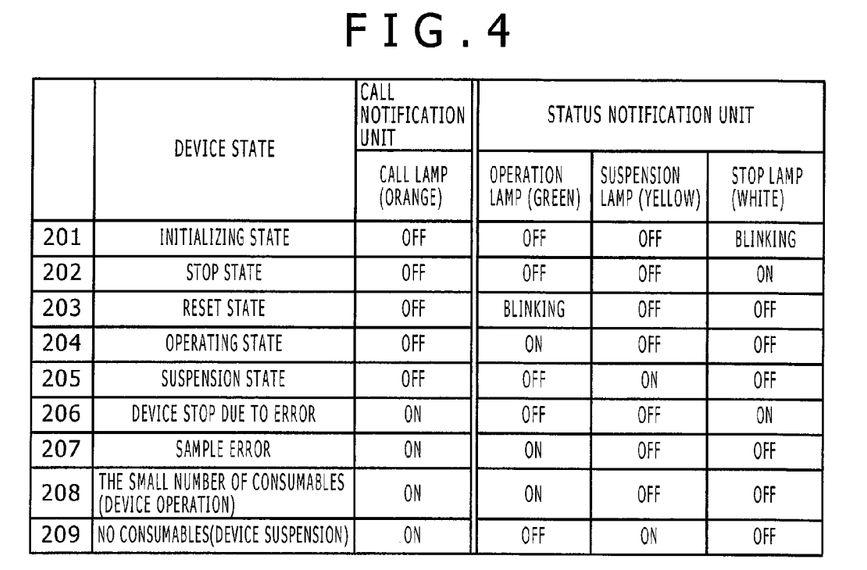
FIG. 4 illustrates the details of a state display.

FIG. 4 illustrates an example of a table representing information notified by the display lamp 90. First, a relationship between the display of the status notifying unit and the operating state of the device will be described.

When the device is powered up, the device first conducts initialization operation. An initialization state 201 is displayed by blinking the stop lamp 10. Upon completion of the initialization, the device is put into a standby state 202, the reception of a signal of operation start starts, and the display lamp 90 turns on the stop lamp 10.

A reset state 203 is a state in which a sample left within the device is discharged, or a movable unit travels to a home position, for transition from the standby state to the operation state, and the display lamp blinks the operation lamp 8. An operation state 204 is a state in which reset operation is completed, and the device operates, and the display lamp 90 turns on the operation lamp 8. A suspension state 205 turns on the suspension lamp 9.

Subsequently, the combination of displays of the call notification unit and the status notifying unit will be described.

Reference numeral 206 is a display of the display lamp 90 in a device emergency stop state. This state corresponds to a case in which a sample from which a bar code label is peeled off is input in error, jamming occurs within the device, and the device urgently stops. Because the error occurs, the device requests the intervention of the operator, and turns on the call lamp 7 of the call notification unit, which is installed in the display lamp 90. Also, because of the state in which the device urgently stops, the status notifying unit turns on the stop lamp 10. With the combination of the call notification unit and the status notifying unit, the operator can recognize that the device urgently stops due to the error, from the display of the display lamp 90 at a glance. For that reason, the operator can urgently cope, with the error of the device.

Reference numeral 202 indicates a stop state of the device. This state corresponds to a case in which another operator has already started the work, and there is no need to call another operator once again. Even if the stop lamp 10 is on in the status notifying unit like the display 206, since the call lamp 7 of the call notification unit is off unlike the display 206, the operator can recognize that there is no need to go to the device.

Reference numeral 207 is a display of the display lamp 90 when the sample error occurs. This display corresponds to a case in which a foreign matter such as fibrin is present within a sample container, and a nozzle is clogged during a dispensing process. Because the occurrence of the sample error requires the intervention of the operator, the device turns on the call lamp 7. Also, in this situation, because the device continues to be in the operation state, the status notifying unit is in a state where the operation lamp 8 is on, indicating that the device is operating. The operator can recognize at a glance that although the device requests the operator's intervention by the combination of the displays of the call notification unit and the status notifying unit, the operator may not immediately cope with the request because of the operation state. For that reason, the operator can execute the works in the order from the higher priority.

Reference numeral 208 is a display of the display lamp 90 when the number becomes smaller than a set value. The device turns on the call lamp 7 because the remaining number of consumables is decreased. Because the device in the operation state, the status notifying unit is in the on-state of the operation lamp 8 indicating that the device is operating. Because the operator can recognize at a glance that the device is operating by the combination of lighting of the call notification unit and the status notifying unit, the operator can execute the works in the order from the higher priority.

Reference numeral 209 is a display of the display lamp 90 when the remaining number of consumables is decreased. Because the replenishment of consumables is necessary, the call notification unit turns on the call lamp 7. Also, when the consumables are finished up, because the device transitions from the operation state to the suspension state, the status notifying unit turns off the operation lamp 8, and turns on the suspension lamp 9 indicative of the suspension. Because the operator understands that the device which calls the operator is in the suspension state by the combination of the call notification unit and the status notifying unit, the operator can recognize at a glance the call that the operator can easily cope with not abnormality of the operator, but the supply of the consumables. For that reason, the operator can execute the works preferentially from the work more difficult to cope with, such as the emergency stop of the device.

Thus, because the display lamp 90 installs the call lamp 7 that requests the intervention of the operator, and the operation lamp 8, the suspension lamp 9, and the stop lamp 10 which indicate the device status therein, the operator can determine at a glance the summary of the operator call by the combination of the lighting. For that reason, the operator can execute the works in the order from the higher priority, and the efficiency of the operator work can be improved.

Because the display lamp 90 executes the display with four different colors of orange, green, yellow, and white, the operator can identify the state of the device from the colors of the lighting LED blocks, and the combination thereof. Also, the call lamp 7, the operation lamp 8, the suspension lamp 9, and the suspension lamp 9 are installed at different positions within the display lamp 90 in order from the left, and all of those lamps are aligned in the same order in the display lamps of the respective modules. For that reason, the state of the respective modules can be identified by the positions within the display lamps of the lighting LED block, and the combination thereof, and the state of the device can be identified even by an operator of color weakness.

Subsequently, a description will be given of the operation of the call clear switch 2, the start switch 3, the suspension switch 4, and the stop switch 5 in the display lamp 90.

When any switch is depressed by the operator, the control unit displays the acceptance of the input by lighting or blinking the LEDs within the switches, and transitions, and transitions to the device state corresponding to the device state and the input switch.

The call clear switch 2, the start switch 3, the start switch 3, and the stop switch 5 correspond to the call lamp 7, the operation lamp 8, the suspension lamp 9, and the stop lamp 10 one-on-one, and are located on the lower portions of the respective lamps. For that reason, a relationship between the operation of the switches and the device state is easily understandable.

Figure 5:
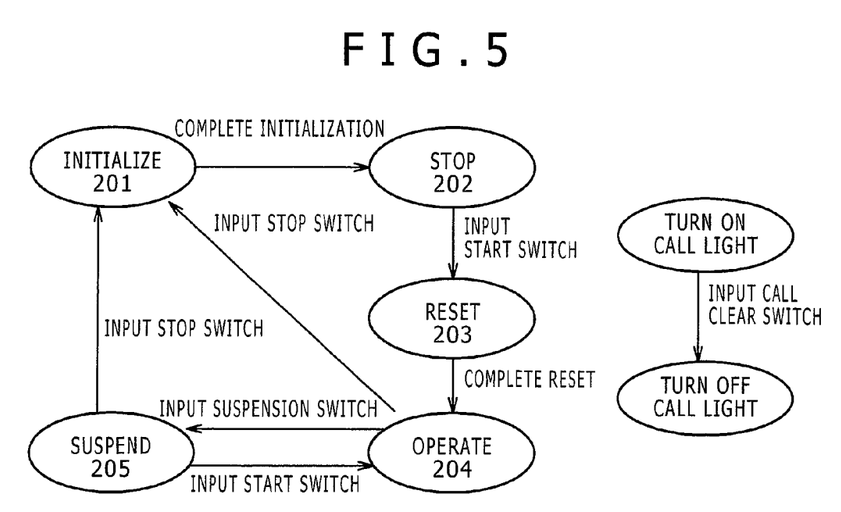
FIG. 5 illustrates a state transition of a device by switch input of the display lamp.

FIG. 5 is a diagram illustrating the transition of the device operation state to the switch input. This transition will be described.

When the operator's intervention in the device is necessary, and the call lamp 7 is lighted, the call clear switch 2 is depressed whereby the device cancels the call displayed in the call lamp 7, and transitions the call lamp 7 from the on-state to the off-state.

The start switch 3, the suspension switch 4, and the stop switch 5 are device status operation switches. The device transitions to the respective statuses corresponding to the operation state, the suspension state, and the stop state according to the input of those switches.

When the device is in the stop state 202, upon accepting the input of the start switch 3, the device transitions the status to the operation state 204. In the status transition, because the device has no information on what is the state of a mechanism within the device, the device initializes a position of the mechanism within the device through the reset state 203. After the completion of the reset operation, the device becomes in the operation state 204.

When the device of the operation state 204 accepts the input of the stop switch 5, the device transitions the status to the stop state 202. In this state transition, the device transitions to the initialization state 201, and becomes in the stop state 202 after the completion of the initialization operation.

Also, when the device of the operation state 204 accepts the input of the suspension switch 4, the device transitions the status to the suspension state 205.

When the device of the suspension state 205 accepts the input of the start switch 3, because the device of the suspension state 205 has positional information on the mechanism within the device, the device transitions to the operation state 204 without conducting the reset operation. Also, when the device of the suspension state 205 accepts the input of the stop switch 5, the device to the stop state 202 through the initialization state 201.

Thus, in the stop (stop state 202) of the device by the operation of the operator, only the lighting of the stop lamp is displayed. On the contrary, in the device emergency stop state by the error of the display 206, the display lamp 90 becomes in a state where the call lamp 7 and the stop lamp 10 are on. Because the operator can recognize the state as the combination of the display of the call notification unit and the display of the status notifying unit, the operator can identify whether the device is stopped by the operation of the operator, or stopped by the occurrence of the error.

Figure 6:
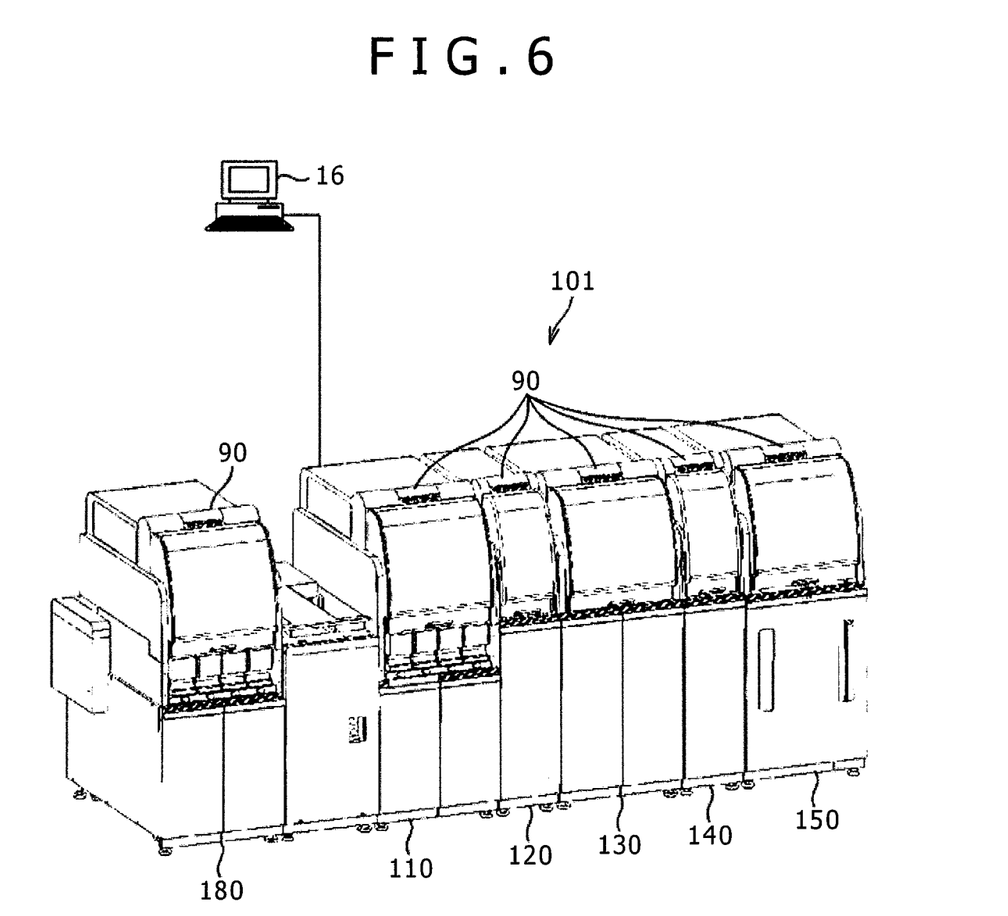
FIG. 6 is a configuration diagram of an overall laboratory automation system.

Subsequently, a description will be given of a laboratory automation system in which the display lamp is installed in the respective modules according to this embodiment.

FIG. 6 illustrates a configuration example of the laboratory automation system according to one embodiment. A laboratory automation system 101 according to this embodiment includes a sample input module 110, an opening module 120, a bar code labeling module 130, a cap supply module 140, a dispensing module 150, a sample storage module 180, the host computer 16, and the display lamp 90.

The input module 110 is a portion that carries in the sample from the external, which is an inlet of the sample in the laboratory automation system 101.

The opening module 120 removes a cap from the sample into a state where the sample can be sorted in the dispensing module, and input to the automated analytical device.

The bar code labeling module 130 is a portion where a bar code for identifying the sample is printed and labeled on an empty test tube used when sorting the sample by the dispensing module, and supplied to the dispensing module 150.

The cap supply module 140 is a portion that automatically supplies a sample cap for sorting the sample into small quantity to the dispensing module 150.

The dispensing module 150 is a portion that sorts the original sample into a plurality of containers supplied from the bar code labeling module 130 or the cap supply module 140.

The storage module 180 is a portion that classifies the sample for each intended purpose, and stores and carries out the sample.

After the sample is taken into the system from the sample input module 110, the sample stops in the opening module 120, the bar code labeling module 130, and the dispensing module 150, and then travels toward the sample storage module 180. The analytical device is connected to the system depending on the system, and in this case, a part of the sample passes through a transport unit (not shown) from the dispensing module 150, is transported to the automated analytical device (not shown), and subjected to a variety of analyzing processes.

The display lamp 90 is mounted on an upper portion of each module of the laboratory automation system at a portion capable of being recognized from a front surface, a back surface, and a top surface thereof. The display lamp 90 notifies the operator of the status of the module on which the display lamp 90 is installed, and the occurrence status of the call. For that reason, the operator can conduct the status identifications of the respective modules at a glance such as the specification of an error occurrence module. Also, because the operation switches are installed in the display lamps 90 of the respective modules, the operator operates the operation switch of the display lamp 90 of the module after the operation of restoring the module in which an error occurs. As a result, the operator can restore the device to the operation state even if the operator does not travel to the operation unit PC, and the work efficiency of the operator is improved.

In the laboratory automation system 101, the operation of the display lamp 90 when an error caused by the sample occurs will be described.

Each module of the laboratory automation system 101 is provided with means (not shown) for reading the bar code labeled on the sample for identifying the sample. There occurs the error caused by a problem with the sample such that a bar code read error occurs, or dispensing fails due to the sample shortage or nozzle clogging in the dispensing module 150. In this case, the device discharges the sample in which the error occurs as the error sample, and transports the sample to an error sample discharge destination registered for each type of the errors. The discharge destination of the error sample includes the storage module 180 and the input module 110. In the system can be registered a sample tray (not shown) of the module of the discharge destination for each type of the errors. In this situation, the device controls the call lamp of the display lamp 90 in the module in which the sample error occurs and the call lamp of the display lamp 90 in the module in which the sample is discharged to turn on at the same time at timing of carrying out the error sample to the carry-out destination module.

Figure 7:
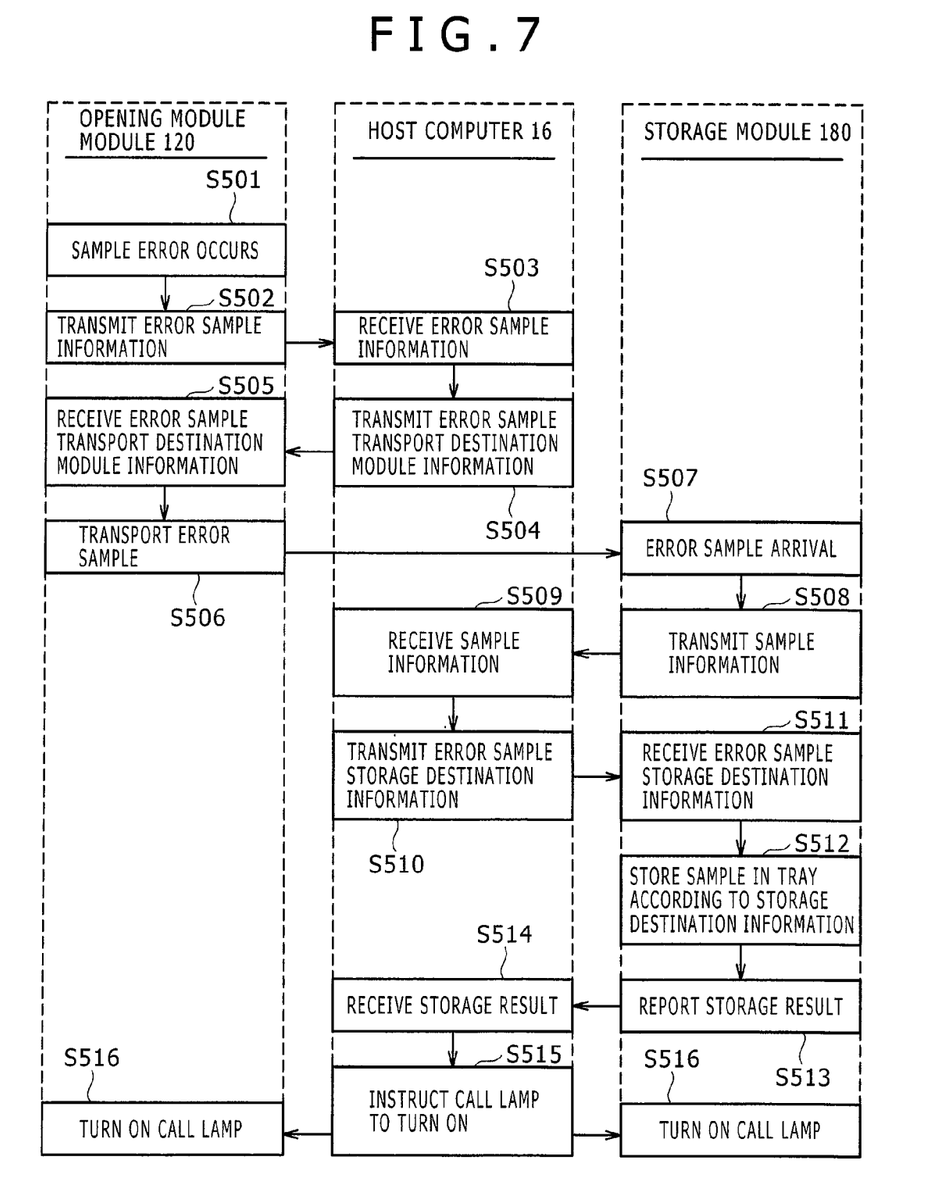
FIG. 7 illustrates a call display operation sequence when a sample error occurs.

A description will be given of an operation sequence of the call display when the error sample in which the bar code read fails in the opening module 120 occurs, and the error sample is carried out to the storage module 180 with reference to FIG. 7. When the error sample in which the opening fails in the opening module 130 occurs (S501), the opening module 120 transmits error sample occurrence information to the host computer 16 (S502). The host computer 16 receives and saves the information on the error sample (S503), and returns the information on the error sample discharge destination registered according to each type of the errors to the opening module 120 (S504). The opening module 120 receives the information on the error sample discharge destination (S505), and transports the error sample to the storage module 180 of the carry-out destination (S506). When accepting the transported sample (S507), the storage module 180 reads the bar code of the sample, and inquires of the host computer about a sample storage destination (S508). In response to this inquiry, the host computer 16 transmits the storage destination of the error sample to the module 180 (S509). The storage module 180 receives the error sample storage destination information (S510), and stores the error sample in a tray according to the information (S511). The storage module 180 informs the host computer 16 about the storage result (S512). After the host computer 16 has received the storage result (S513), the host computer 16 transmits a call lamp lighting instruction to the display lamp 90 of the bar code labeling module 130 in which the error sample occurs, and the display lamp 90 of the storage module 180 which is the carry-out destination of the error sample (S515). The two modules that have received the call lamp lighting instruction light the two call lamps 7 of the respective display lamps 90 at the same timing, and display the module in which the error occurs, and the module of the carry-out destination (S516).

Figure 8:
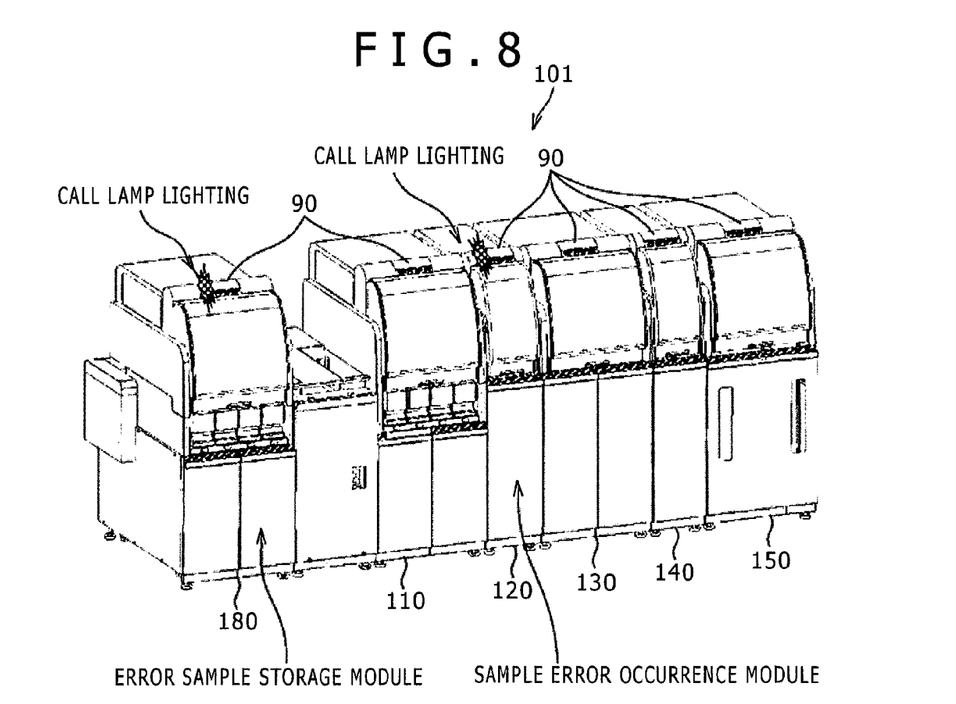
FIG. 8 illustrates a combination of displays between modules.

FIG. 8 illustrates a state in which the sample error occurs in the opening module 120, and the laboratory automation system 101 in which the error sample is stored in the storage module 180 displays the sample error, and the operator call lamps 7 of the display lamps 90 in the opening module 120 and the storage module 180 turn on are lighted at the same time. In this example, the combination of the module in which the error occurs, and the module of the carry-out destination is configured by the opening module 120 and the storage module 180. However, the combination of the other modules may be applied.

Figure 9:
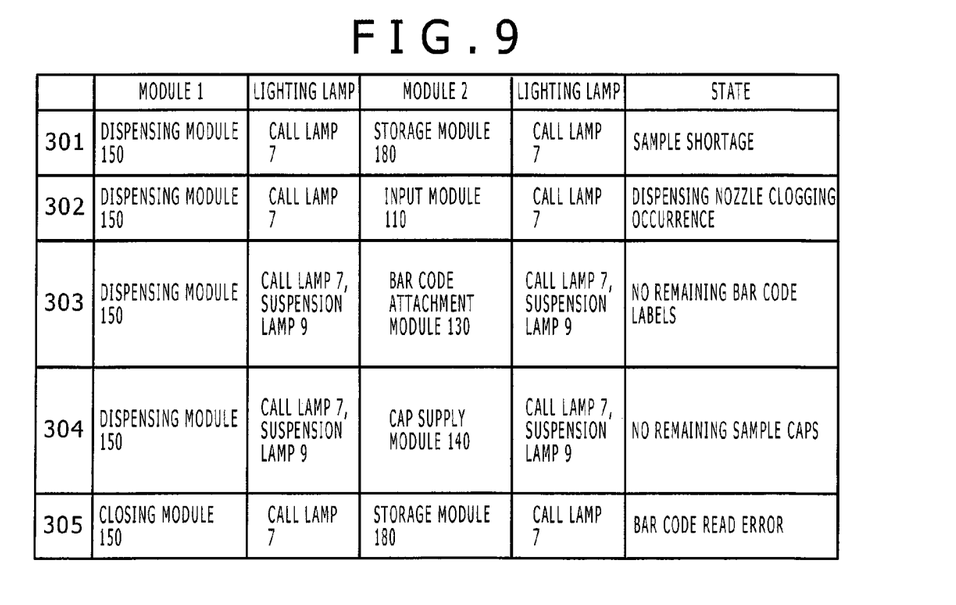
FIG. 9 illustrates the combination of the displays between the modules.

FIG. 9 illustrates the combination of the displays between the modules. Reference numeral 301 indicates the combination of the displays when the sample error of the sample shortage occurs in the dispensing module 150, and is stored in the storage module 180, which is represented by the combination of the lighting of the call lamps 7 in the two modules.

Reference numeral 302 indicates the combination of the displays when the sample error of the nozzle clogging occurs in the dispensing module 150, and is stored in the input module 110, which is represented by the combination of the lighting of the call lamps 7 in the two modules.

Reference numeral 303 represents the combination of the displays when the remaining number of the bar codes is finished up in the bar code labeling module 130, and the dispensing operation of the dispensing module 150 is suspended, which is displayed by the combination of the lighting of the call lamp 7 and the suspension lamp 9 in the two modules.

Reference numeral 304 denotes the combination of the displays when the sample caps are finished up in the cap supply module 140, and the dispensing operation of the dispensing module 150 is suspended, which is displayed by the combination of the call lamp 7 and the suspension lamp 9 in the two modules.

Reference numeral 305 denotes the combination of the displays when the sample error of the bar code read occurs in the opening module 120, and is stored in the storage module 180, which is displayed by the combination of the lighting of the call lamps 7 in the two modules.

Because the displays of the display lamps 90 in the plurality of modules are combined together to notify the information, the operator can visually recognize the module in which the error occurs and the discharge destination of the error sample at a glance, and can know the type of error according to those information. Since the type of error is known, a troublesome for confirming the error contents in the operation PC can be omitted. Also, since the type of error is known, the degree of urgency of processing the error sample can be recognized, and the operator can execute the work to be conducted preferentially. As a result, the operator can efficiently execute the work.

Also, since the operator can recognize the carry-out destination of the error sample at a glance, there is no need to check the carry-out destination, that is, to which of the plural carry-out destinations the error sample is carried out. For that reason, the work efficiency of the operator is improved. Also, if the error occurs in the sample such as the emergency sample which needs to be processed as soon as possible, the process can be accelerated by the operator.

In this embodiment, the laboratory automation system is exemplified. However, the present invention is not limited to this embodiment. For example, there may be applied an automated analytical system in which a plurality of analytical devices is coupled to each other to improve the processing efficiency. Further, there may be applied a system in which the laboratory automation system and the automated analytical device are coupled to each other. In this case, as in the present invention, each unit is provided with the call notification unit and the status notifying unit so that the operator can confirm the degree of urgency of the coping even from a distance.

Also, in this embodiment, the display lamp is provided as the notifying means, but in order to enable notification to the operator distant from the device, other means may be applied. For example, sound may be emitted from a speaker. Also, the speaker and the display lamp may be used together. With the use of sound for notification, information from the device can be notified the operator who cannot visually recognize the device, for example, who faces away from the device.

LIST OF REFERENCE SIGNS 1 display unit cover
2 call clear switch
3 start switch
4 suspension switch
5 stop switch
6 partition plate
7 call lamp
8 operation lamp
9 suspension lamp
10 stop lamp
11 connector
12 waterproof cover
13 I/O board
14 control unit
15 CPU
16 host computer
90 display lamp
101 laboratory automation system

The invention claimed is:

1. A laboratory automation device or an automated analytical device, comprising:
   a plurality of processing modules that process samples, each of the processing modules operating independently; and
   a transporting device that transports samples between said plurality of processing modules;
   wherein at least two of the processing modules each have:
      a notifying unit mounted thereon and having a status notifying illumination device that notifies a consumables status or a processing module status of the corresponding processing module, and a call notification illumination device that notifies a call state which indicates whether or not the corresponding processing module requires intervention by an operator;
      a plurality of input switches mounted thereon and disposed adjacent to the notifying unit and each switch having a one to one relationship with one of the status notifying illumination device and the call notification illumination device of the notifying unit, respectively; and
      a controller programmed to:
      control the status notifying illumination device or the call notification illumination device to independently provide notification at the same time or at different times, wherein the controller is programmed to control the status notifying illumination device and the call notification illumination device automatically based on the status of the corresponding processing module, and wherein the controller is further programmed to control the status notifying illumination device and the call notification illumination device based on a selection of an input from at least one of the plurality of input switches; and
      control a status of the corresponding processing module upon receiving the input from the at least one of the plurality of input switches of the corresponding processing module, and, upon an occurrence of an error at the corresponding processing module, control the notifying unit to produce a notification of the error at the corresponding processing module.

2. The laboratory automation device or an automated analytical device according to claim 1,
   wherein the status notifying illumination device includes a plurality of notifying illumination devices that notifies of at least one of an operating state, a suspension state, and a stop state of the corresponding processing module.

3. The laboratory automation device or an automated analytical device according to claim 1,
   wherein the status notifying illumination device and the call notification illumination device include a plurality of illuminators, and wherein the controller is further programmed to cause the illuminators of the call notification illumination device and the status notifying illumination device to turn ON, blink or turn OFF.

4. The laboratory automation device or an automated analytical device according to claim 3,
wherein the controller is further programmed to cause the illuminator to blink while the corresponding processing module is transitioning from one state to another state.

5. The laboratory automation device or an automated analytical device according to claim 1,
wherein the plurality of input buttons include at least one of a call clear button that clears a call state, a start button that transitions the corresponding processing module from a suspension state or a stop state to an operating state, a suspension button that temporarily suspends the corresponding processing module from the operating state, and a stop button that transitions the respective processing module from the operating state or the suspension state to the stop state,
wherein the start state, suspension state and stop state indicate the processing module status.

6. The laboratory automation device or an automated analytical device according to claim 1,
wherein the input buttons each include an illuminator, and
wherein each of the at least two of the processing modules have a control circuit that turns ON, blinks, and turns OFF the corresponding illuminator according to an input from the input buttons.

7. The laboratory automation device or an automated analytical device according to claim 1, wherein the processing modules are coupled with each other.

8. The laboratory automation device or automated analytical device according to claim 1, wherein the plurality of illuminators are comprised of light-emitting diodes (LEDs).

* * * * *